US009066653B2

(12) United States Patent
Mihaljevic et al.

(10) Patent No.: US 9,066,653 B2
(45) Date of Patent: Jun. 30, 2015

(54) DEVICES, SYSTEMS, AND METHODS FOR VISUALIZING AND MANIPULATING TISSUE

(71) Applicant: THE CLEVELAND CLINIC FOUNDATION, Cleveland, OH (US)

(72) Inventors: Tomislav Mihaljevic, Gates Mills, OH (US); Shengqiang Gao, Beachwood, OH (US); Kiyotaka Fukamachi, Mayfield Hts., OH (US); Mariko Kobayashi, Cleveland, OH (US); Eugene J. Jung, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 153 days.

(21) Appl. No.: 13/789,953

(22) Filed: Mar. 8, 2013

(65) Prior Publication Data
US 2013/0237817 A1    Sep. 12, 2013

Related U.S. Application Data

(60) Provisional application No. 61/608,169, filed on Mar. 8, 2012.

(51) Int. Cl.
| | |
|---|---|
| *A61B 6/00* | (2006.01) |
| *A61B 1/00* | (2006.01) |
| *A61B 1/005* | (2006.01) |
| *A61M 25/00* | (2006.01) |
| *A61M 25/04* | (2006.01) |
| *A61B 17/00* | (2006.01) |

(52) U.S. Cl.
CPC ......... *A61B 1/00089* (2013.01); *A61B 1/00085* (2013.01); *A61B 1/0051* (2013.01); *A61M 25/0074* (2013.01); *A61M 25/04* (2013.01); *A61B 2017/00243* (2013.01); *A61B 2217/007* (2013.01)

(58) Field of Classification Search
CPC .......... A61B 1/00089; A61B 1/00085; A61B 2017/00243; A61B 2217/007; B61B 1/0051; A61M 25/0074; A61M 25/04
USPC .................................................. 600/407–480
See application file for complete search history.

(56) References Cited

U.S. PATENT DOCUMENTS 4,619,247 A * 10/1986 Inoue et al. ................... 600/116
4,784,133 A * 11/1988 Mackin ............................ 606/7

(Continued)

FOREIGN PATENT DOCUMENTS

WO    2008008796 A2    1/2008

OTHER PUBLICATIONS

PCT International Search Report and Written Opinion, mailed Jul. 5, 2013, pp. 1-13.

*Primary Examiner* — Sanjay Cattungal
(74) *Attorney, Agent, or Firm* — Tarolli, Sundheim, Covell & Tummino LLP

(57) ABSTRACT

One aspect of the present disclosure relates to a tissue imaging device that includes a catheter body, a hood, and a visualization assembly. The catheter body includes a distal end portion, a proximal end portion, and at least one lumen extending between the distal and proximal end portions. The catheter body includes at least one drainage port having a first opening and at least one infusion port having a second opening. The first and second openings are located about a lateral aspect of the catheter body. The hood projects distally from the distal end portion and is configured to self-expand into an expanded deployment state that defines an open area therein. The visualization assembly is disposed within the open area and extends distally from the distal end portion of the catheter body.

9 Claims, 17 Drawing Sheets

(56) References Cited

U.S. PATENT DOCUMENTS

| | | | |
|---|---|---|---|
| 6,979,290 B2 * | 12/2005 | Mourlas et al. | 600/115 |
| 7,534,204 B2 | 5/2009 | Starksen et al. | |
| 7,918,787 B2 * | 4/2011 | Saadat | 600/129 |
| 2007/0167828 A1 * | 7/2007 | Saadat | 600/463 |
| 2008/0009747 A1 * | 1/2008 | Saadat et al. | 600/471 |
| 2008/0015569 A1 * | 1/2008 | Saadat et al. | 606/41 |
| 2011/0054326 A1 * | 3/2011 | Barnett | 600/453 |

* cited by examiner

DEVICES, SYSTEMS, AND METHODS FOR VISUALIZING AND MANIPULATING TISSUE

RELATED APPLICATION

This application claims the benefit of U.S. Provisional Patent Application Ser. Nos. 61/608,169, filed Mar. 8, 2012, the entirety of which is hereby incorporated by reference for all purposes.

TECHNICAL FIELD

The present disclosure relates generally to medical devices, systems, and methods for visualizing and/or manipulating regions of tissue within a body and, more particularly, to devices, systems, and methods for visualizing and/or manipulating cardiac tissue regions, such as tissues surrounding or adjacent a heart valve, which are generally difficult to image because of surrounding opaque bodily fluids.

BACKGROUND

Conventional devices for visualizing interior regions of a body lumen are known. For example, ultrasound devices have been used to produce images from within a body in vivo. Ultrasound has been used both with and without contrast agents, which typically enhance ultrasound-derived images. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Other external imaging modalities are also conventionally utilized. For example, computed tomography and magnetic resonance imaging are typical modalities that are widely used to obtain images of body lumens, such as the interior chambers of the heart. Such imaging modalities, however, fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface. Fluoroscopy also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

SUMMARY

One aspect of the present disclosure relates to a tissue imaging device that includes a catheter body, a hood, and a visualization assembly. The catheter body includes a distal end portion, a proximal end portion, and at least one lumen extending between the distal and proximal end portions. The catheter body includes at least one drainage port having a first opening and at least one infusion port having a second opening. The first and second openings are located about a lateral aspect of the catheter body. The hood projects distally from the distal end portion and is configured to self-expand into an expanded deployment state that defines an open area therein. The visualization assembly is disposed within the open area and extends distally from the distal end portion of the catheter body.

Another aspect of the present disclosure can include a system for imaging a tissue. The system can comprise a device and an occlusion catheter. The device can include a catheter body, a hood, and a visualization assembly. The catheter body can include a distal end portion, a proximal end portion, and at least one lumen extending between the distal and proximal end portions. The catheter body can include at least one drainage port having a first opening and at least one infusion port having a second opening. The first and second openings can be located about a lateral aspect of the catheter body. The hood can project distally from the distal end portion and be configured to self-expand into an expanded deployment state that defines an open area therein. The visualization assembly can be disposed within the open area and extend distally from the distal end portion of the catheter body. The occlusion catheter can comprise a main body and an inflation member. The main body can have a distal end portion, a proximal end portion, and a lumen that extends between the distal and proximal end portions. The inflation member can be operably disposed about the distal end portion and be configured to selectively transition between expanded and collapsed configurations. The inflation member can have an outer surface configured to sealingly contact a luminal surface of a blood vessel when the inflation member is in the expanded configuration.

Another aspect of the present disclosure can include a method for imaging an immersed region of tissue. One step of the method can include providing a device that includes a catheter body, a hood, and a visualization assembly. The catheter body can include a distal end portion, a proximal end portion, and at least one lumen extending between the distal and proximal end portions. The catheter body can include at least one drainage port having a first opening and at least one infusion port having a second opening. The first and second openings can be located about a lateral aspect of the catheter body. The hood can project distally from the distal end portion and be configured to self-expand into an expanded deployment state that defines an open area therein. The visualization assembly can be disposed within the open area and extend distally from the distal end portion of the catheter body. The hood can be positioned against or adjacent the region of tissue to be imaged. Next, a translucent imaging fluid can be urged into the open area of the hood via the second opening such that an opaque fluid is displaced from within the open area into the environment external to the hood. The region of tissue can then be visualized through the translucent imaging fluid using the visualization assembly.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1A:
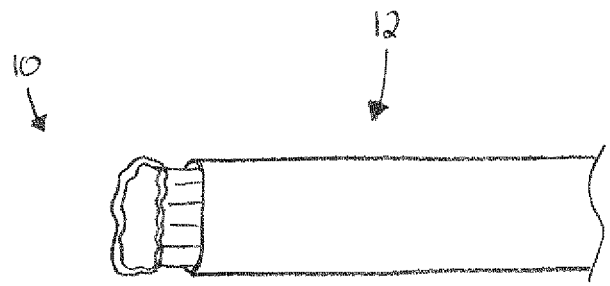
FIG. 1A is a perspective view showing a tissue imaging device in a low-profile delivery configuration constructed in accordance with one aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can be used interchangeably with the term "patient" and refer to any warm-blooded organism including, but not limited to, human beings, pigs, rats, primates, mice, dogs, goats, sheep, horses, cattle, etc.

Overview

The present disclosure relates generally to medical devices, systems, and methods for visualizing and/or manipulating regions of tissue within a body and, more particularly, to devices, systems, and methods for visualizing and/or manipulating cardiac tissue regions, such as tissues surrounding or adjacent a heart valve, which are generally difficult to image because of surrounding opaque bodily fluids. The ability for surgeons to visualize target tissue structures and accurately operate thereon is a critical determinant in the success of a given operation. Visualizing a target tissue structure, however, is typically only possible with open surgical procedures (e.g., open heart surgery). Such surgeries entail a high degree of risk (e.g., nosocomial infection) and are taxing on older patients. Percutaneous techniques for visualizing target tissue structures often entail endoscopes modified to deliver fluid (e.g., saline) to assist in visualizing the target structures; however, such devices must operate under high pressures in the heart, and require the introduction of excessive imaging fluid (e.g., saline) into the bloodstream, which creates several undesirable complications, such as hemodilution.

Advantageously, the present disclosure provides minimally invasive devices, systems, and methods for visualizing and/or manipulating regions of tissue (e.g., cardiac tissue) that, in some instances, avoid hemodilution by keeping the pressure inside the heart at a relatively low threshold (e.g., about 15-20 mm Hg). Consequently, the use of a hemoconcentrator to filter out an imaging fluid is largely eliminated. Additionally, the present disclosure provides devices, systems, and methods that enable optical visualization of moving structures within a beating heart and provide a medical practitioner (e.g., a cardio-thoracic surgeon or interventional cardiologist) a clear view of the moving structures to aid the diagnosis of disease and/or provide real-time imaging for therapy guidance.

Devices

One aspect of the present disclosure can include a device 10 (FIGS. 1A-B) for imaging and/or manipulating tissue. Tissue that can be imaged and/or manipulated by the device 10 can include any biological structure, such as bones, cavities, lumens, organs, tendons, cartilage, blood vessels, and the like. In some instances, tissue that can be imaged and/or manipulated by the device 10 can include cardiac tissue, such as the epicardium, myocardium or endocardium, or portions thereof, as well as cardiac valves (e.g., an aortic valve, a pulmonic valve, a tricuspid valve, a mitral valve) and other heart structures (e.g., an interatrial septum), including abnormal heart structures, such as a left or right atrial appendage.

Figure 1B:
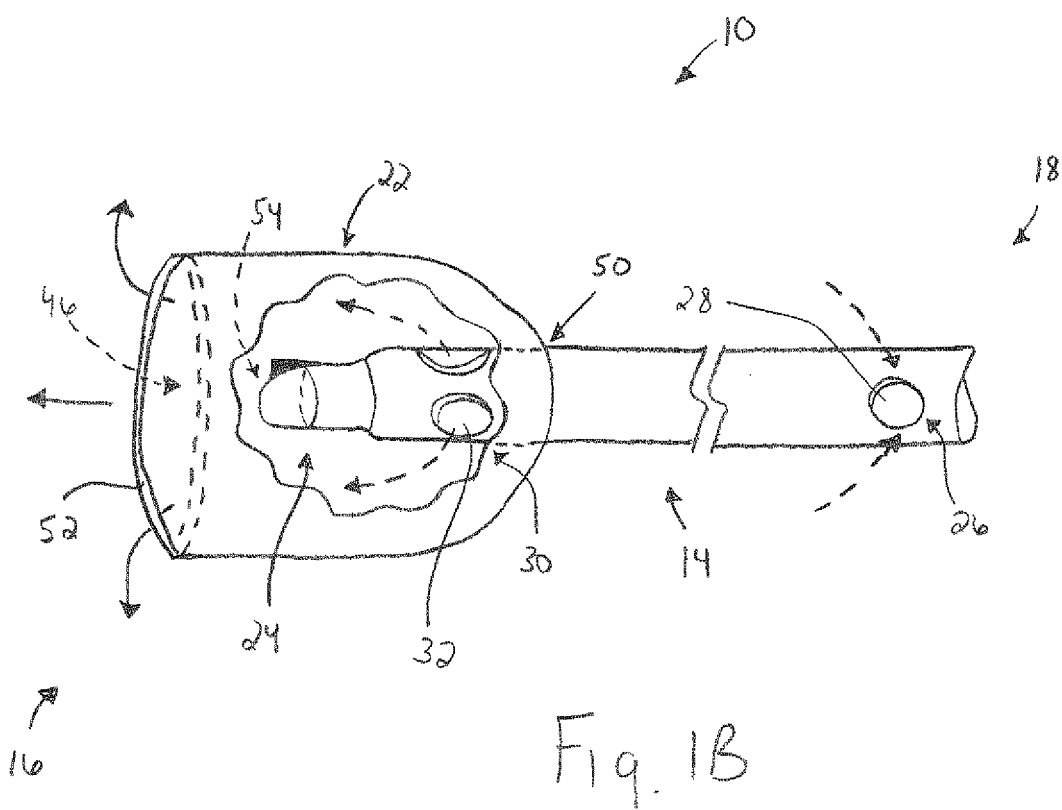
FIG. 1B is a perspective view showing the device in FIG. 1A in an expanded deployment state.

As shown in FIGS. 1A-B, the device 10 is movable from a collapsed configuration (FIG. 1A) to an expanded or deployed configuration (FIG. 1B). In some instances, the device 10 can be at least partly disposed in a delivery catheter 12. As described in more detail below, the delivery catheter 12 can be axially translated over the device 10 to move the device between the collapsed and expanded or deployed configurations. The device 10 can generally comprise a catheter body 14 having a distal end portion 16, a proximal end portion 18, at least one lumen 20 (FIG. 3B) extending between the proximal and distal end portions (FIG. 1B), a hood 22 projecting distally from the distal end portion, and a visualization assembly 24. The device 10 can be shaped and configured for use with minimally invasive procedures, such as a minithoracotomy, subxiphoid (e.g., a left ventricle approach), or femoral artery (e.g., percutaneous) approach. In some instances, the device 10 can be configured for single use as part of a sterilized, single use kit.

Figure 2:
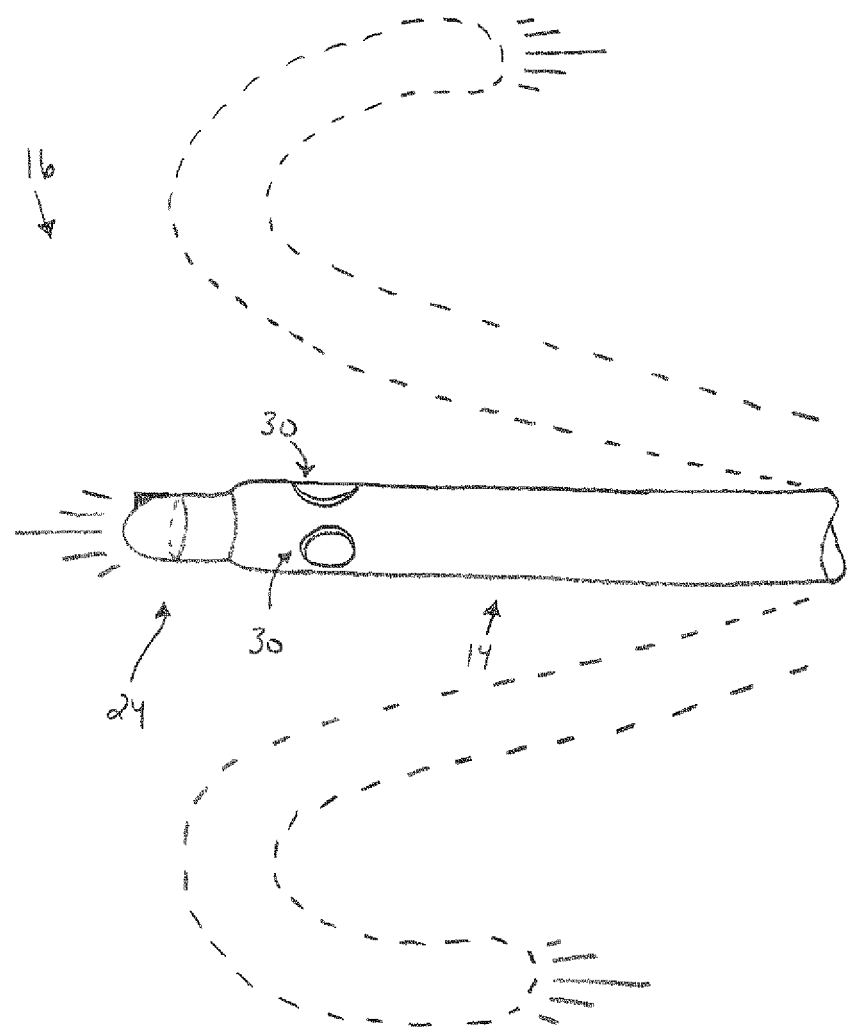
FIG. 2 is a perspective view showing the device in FIGS. 1A-B being retroflexed (dotted lines) (hood omitted for clarity)

In another aspect, the catheter body 14 can have an elongated, tubular configuration. The catheter body can have an outer diameter of 14 Fr; however, it will be appreciated that the catheter body can have a greater or lesser outer diameter depending, for example, on the particular tissue to be imaged and/or the surgical route used to gain access to the tissue. Also depending, at least in part, on the particular tissue to be imaged and/or the surgical route used to gain access to the tissue, the length of the catheter body 14 can be varied as needed. In one example, the length of the catheter body 14 can be about 100 cm. The catheter body 14 can have a torque-bearing construction (e.g., a braided wire) that allows the catheter body to transfer torque and transmit pushing forces (e.g., to permit delivery through an arterial access site into the left ventricle). In some instances, the catheter body 14 can be steered via at least one push-pull wire (not shown). The torque-bearing construction of the catheter body 14 imparts the catheter body with bi-directional steering capability, meaning that the catheter body is articulatable off-axis relative to a longitudinal axis thereof by about 180° in each direction (FIG. 2). The catheter body 14 can be made of any one or combination of biocompatible materials, such as a polyether block amide (e.g., PEBAX). In some instances, the catheter body 14 can be articulatable off-axis relative to the longitudinal axis thereof by more than 180° in each direction.

Figure 3A:
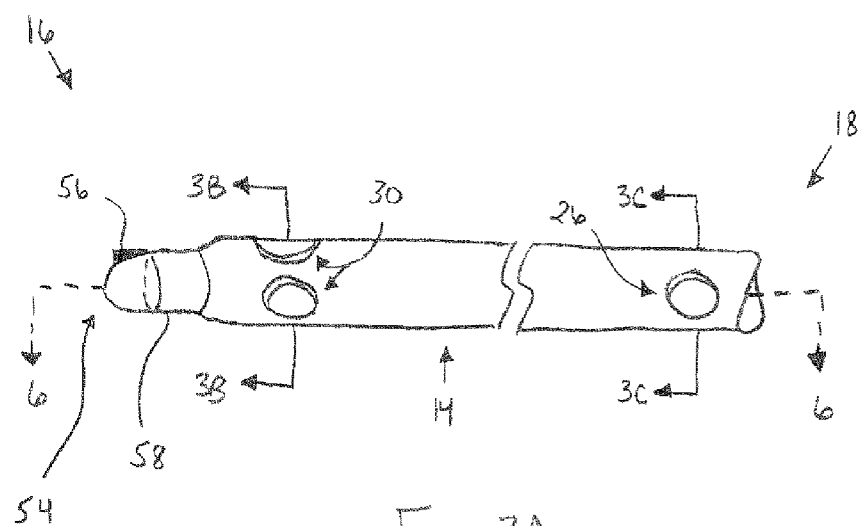
FIG. 3A is a perspective view showing the device in FIGS. 1A-B (hood omitted for clarity)
Figure 3B:
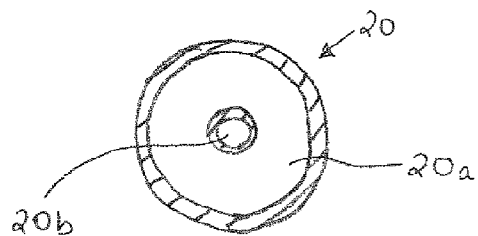
FIG. 3B is a cross-sectional view taken along Line 3B-3B in FIG. 3A.
Figure 3C:
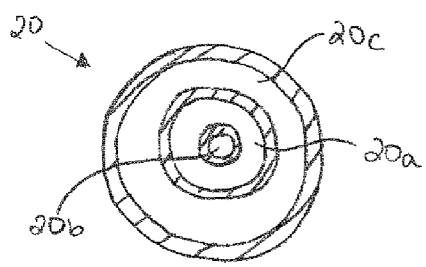
FIG. 3C is a cross-sectional view taken along Line 3C-3C in FIG. 3A.
Figure 3D:
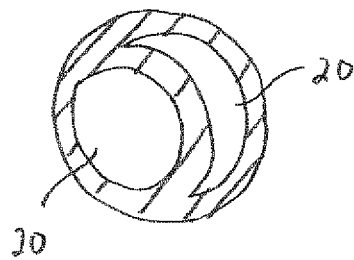
FIGS. 3D-F are cross-sectional views showing alternative configurations of the device in FIG. 3A.
Figure 3E:
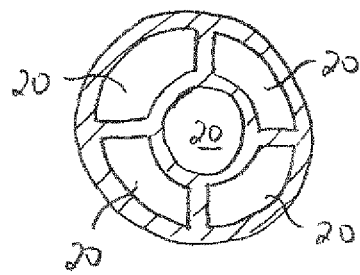
Figure 3F:
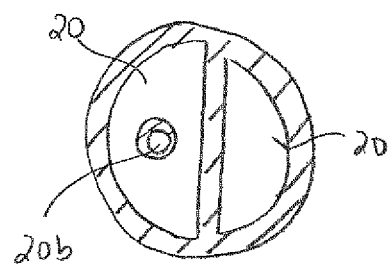
Figure 4A:
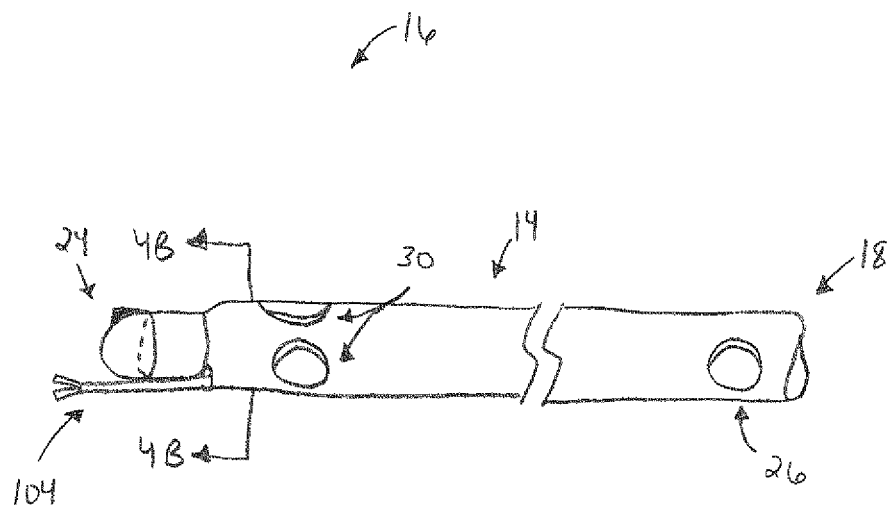
FIG. 4A is a perspective view showing an alternative configuration of the device in FIG. 3A.
Figure 4B:
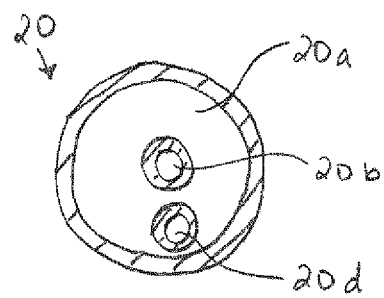
FIG. 4B is a cross-sectional view taken along Line 4B-4B in FIG. 4A.

In another aspect, the catheter body 14 can include at least one lumen 20 (FIGS. 3A-C) extending between the distal and proximal end portions 16 and 18. In some instances, the catheter body 14 can include a lumen 20a configured to convey an imaging fluid therethrough, a lumen 20b configured to convey one or more electronics components (e.g., a fiberoptic wire), a lumen 20c configured to convey an opaque fluid (e.g., blood and/or a mixture of blood and imaging fluid) therethrough, and/or a lumen 20d (FIG. 4B) configured to convey a surgical instrument (FIG. 4A) or medical substance therethrough (e.g., an ablation electrode, a sensor, an annuloplasty ring, an atrial appendage closure device, valve clips, a tissue manipulator, a sealant, an energizable cryo-ablation or laser probe, etc.). As shown in FIGS. 3B-C, different portions of the catheter body 14 can include different lumens 20. For example, a distal section of the catheter body 14 can include a lumen 20b configured to convey one or more electronics components (e.g., wires), and a lumen 20a configured to convey an imaging fluid. In one example, the lumen 20a for conveying an imaging fluid can be shaped and configured to permit fluid flow at a rate of about 1 L/min during operation of the device 10. In such instances, the lumen 20a for conveying an imaging fluid can have a diameter of about 1 cm to about 1.5 mm (or 10-12 Fr) to achieve a flow rate of about 1 L/min at physiological pressures. Additionally, a proximal segment of the catheter body 14 can include a lumen 20b configured to convey one or more electronics components, and a lumen 20c configured to convey an opaque fluid (e.g., blood). In one example, the diameter of the lumen 20c configured to convey the opaque fluid can be greater than the lumen 20a configured to convey the imaging fluid. It will be appreciated that other configurations of the catheter body 14 are possible, such as those in FIGS. 3D-F, which optimize cross-sectional space in the catheter body.

Figure 5:
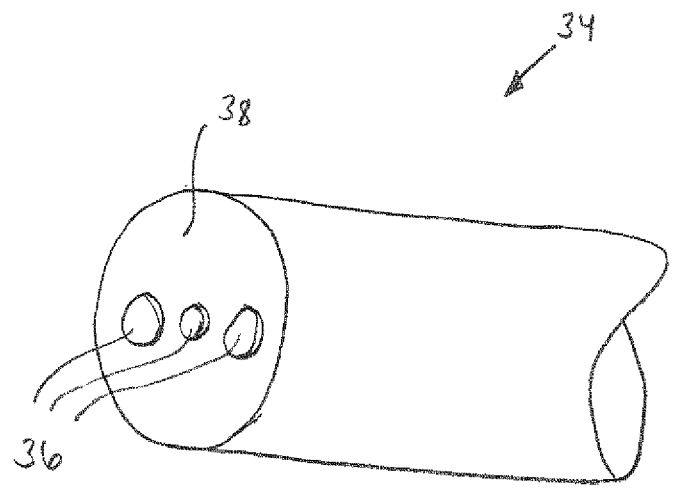
FIG. 5 is a perspective view showing an imaging endoscope or catheter of the prior art.
Figure 6:
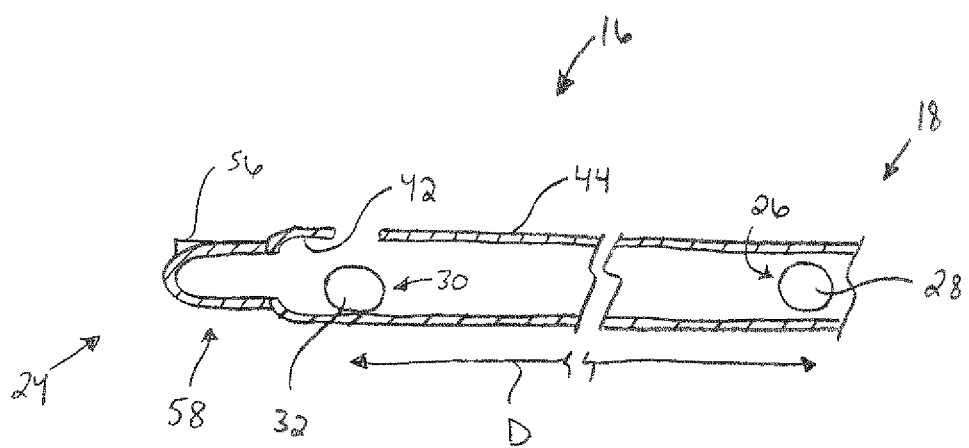
FIG. 6 is a cross-sectional view taken along Line 6-6 in FIG. 3A.

In another aspect, the catheter body 14 can include at least one drainage port 26 having a first opening 28, and at least one infusion port 30 having a second opening 32 (FIG. 6). Each of the drainage and infusion ports 26 and 30 can be located about a lateral aspect of the catheter body 14. In other words, the first and second openings 28 and 32 are substantially parallel with the at least one lumen 20 of the catheter body 14. The drainage and infusion ports 26 and 30 are axially spaced apart from one another by a distance D, which can be varied as needed. In some instances the distance D can be less than about 10 cm, about 15 to about 45 cm, or greater than about 50 cm. The configuration of the drainage and infusion ports 26 and 30 is unlike conventional endoscopes or cardioscopes 34 (FIG. 5), where the openings 36 thereof are flush with the distal surface 38 of the endoscope or cardioscope. The configuration of the device 10, however, advantageously enables high fluid flow and circulation rates to promote rapid and effective tissue visualization, which is not possible using conventional endoscope or cardioscope configurations.

In one example, the at least one drainage port 26 (FIG. 6) can be axially spaced apart from, and located proximal to, the at least one infusion port 30. In such instances, the proximal location of the drainage port 26 relative to the infusion port 30 is advantageous because it avoids short circuiting the imaging fluid. When the device 10 is operably connected with a cardiopulmonary circuit (CPB) 40 (FIG. 16), for example, the drainage port 26 (FIG. 6) can function to drain left ventricular fluid into a CPB venous reservoir at a rate equal to the maximum fluid injection rate of an imaging fluid (e.g., about 0.5 to about 2 L/min).

The drainage and infusion ports 26 and 30 are defined by the first and second openings 28 and 32, respectively, each of which extends between an inner surface 42 and an outer surface 44 of the catheter body 14. In some instances, the drainage port 26 is in fluid communication with a lumen 20*c* configured to convey an opaque fluid through the catheter body 14. In other instances, the infusion ports 30 are in fluid communication with a lumen 20*a* configured to convey an imaging fluid through the catheter body 14. Although the first and second openings 28 and 32 are shown in FIG. 6 as being circular, it will be appreciated that other shapes are possible (e.g., square, rectangular, ovoid, etc.). It will also be appreciated that the catheter body 14 can include any number of drainage and infusion ports 26 and 30. The diameter of each of the drainage and infusion ports 26 and 30 can be the same or different. In one example, the diameter of the drainage port 26 can be greater than the diameter of each of the drainage ports 30. In some instances, the infusion ports 30 can be axially aligned with one another. As shown in FIG. 1B, for example, each of the infusion ports 26 is axially aligned with one another. In other instances, the infusion ports 26 can be axially offset from one another. Where the catheter body 14 includes two or more drainage ports 26, it will be appreciated that each of the drainage ports can be axially aligned with, or axially offset from, the other drainage port(s).

Figure 16:
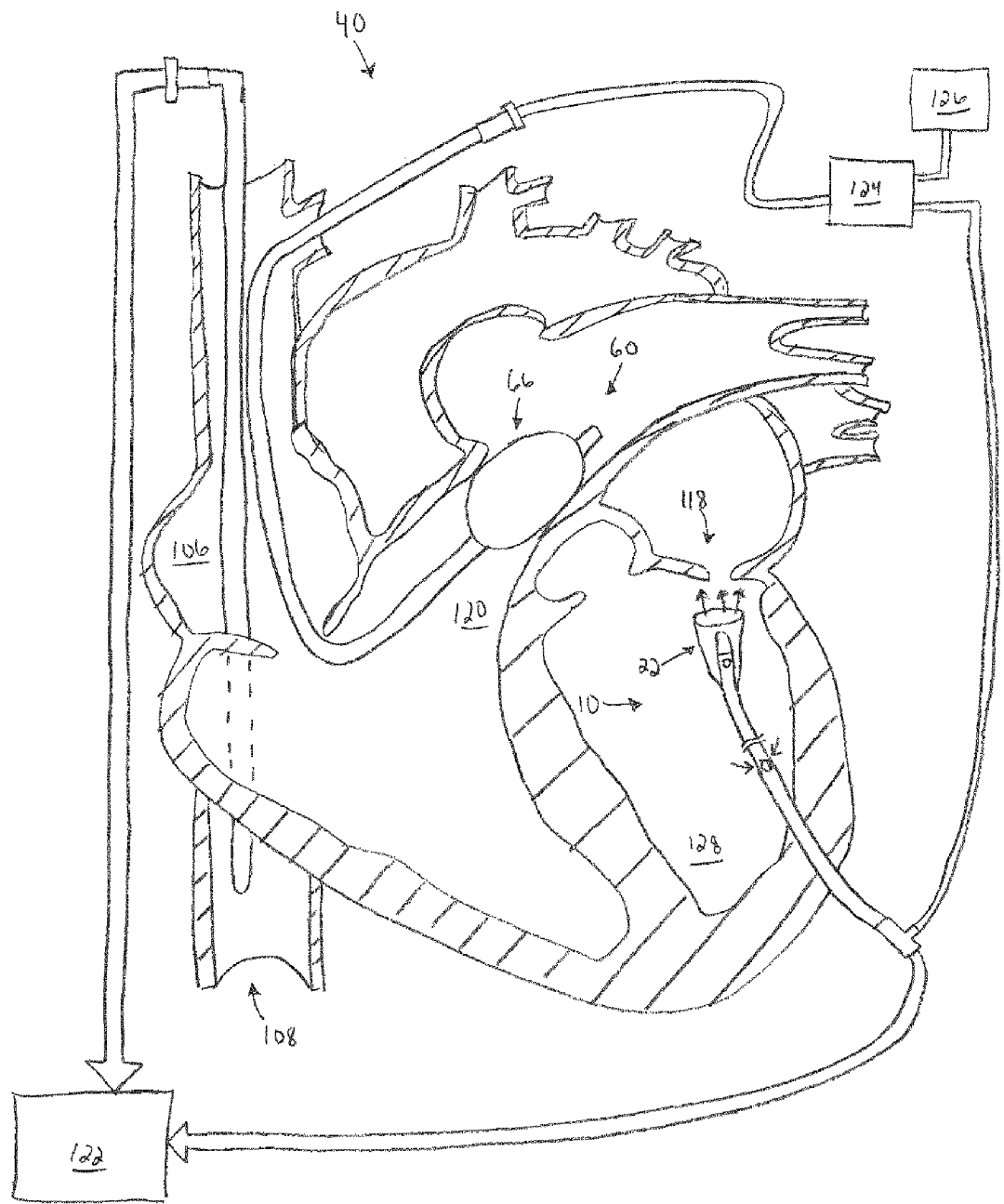
FIG. 16 is a schematic illustration showing use of a system and cardiopulmonary bypass circuit (CPB) to visualize an immersed mitral valve via a trans-apical approach according to the method in FIG. 15.

In another aspect, the proximal end portion 18 of the catheter body 14 can include a handle (not shown) for manipulating or steering the device 10. The handle can have an ergonomic configuration and be made, for example, of an injection molded polymer, such as polycarbonate or polyoxymethylene. In some instances, the handle can include a lever or other mechanism for steering the distal end portion 16 of the device 10. In other instances, the handle can be operably connected to a source of imaging fluid (not shown) and a source of negative pressure or suction (not shown). In one example, a proximal end of the handle can include a T-valve for connection to the imaging fluid source and the suction source. In further instances, the handle can include one or more switches or buttons to activate certain components of the device 10, such as the visualization assembly 24. For example, the handle can include a single switch or button that allows a physician to synchronize flushing with illumination, thereby minimizing fluid introduction into the heart and the need for subsequent drainage. Other components that may be included as part of the handle can include an interconnect from the visualization assembly 24 to a video processor connection, a port for surgical tool insertion, and a port for interconnection to a CPB circuit 40 (FIG. 16).

In another aspect, the device 10 (FIG. 1B) includes a hood 22 that projects distally from the distal end portion 16 of the catheter body 14. The hood 22 is configured to transition from a low-profile delivery configuration (FIG. 1A) to an expanded deployment state (FIG. 1B). In the expanded deployment state, the hood 22 defines an open area 46 therein. The open area 46 is the area within or about which the tissue region of interest may be imaged. As indicated by the arrows in FIG. 1B, the infusion ports 30 are in fluid communication with the open area 46 such that the hood 22 can direct flow of an imaging fluid into a desired field of vision and thereby displace opaque fluids (e.g., from directly in front of visualization assembly 24).

Figure 7A:
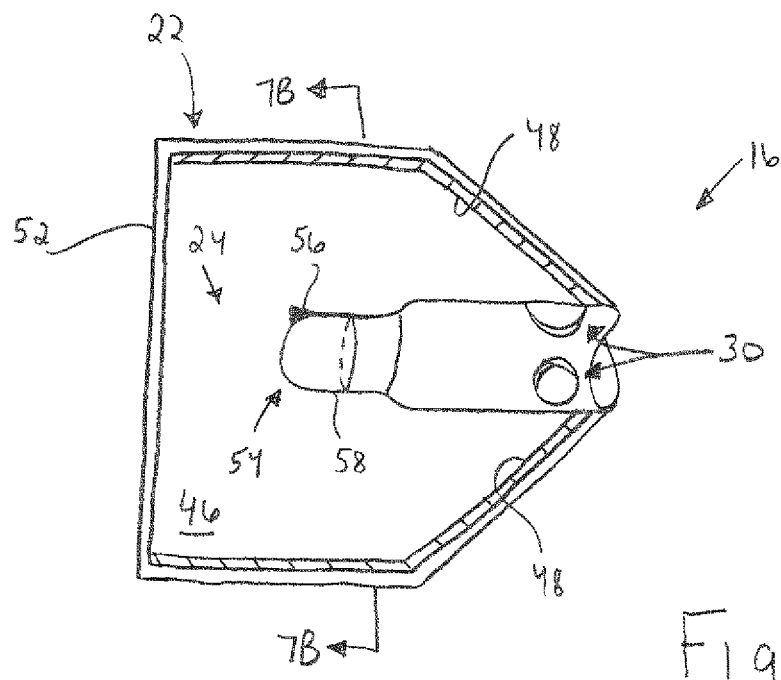
FIG. 7A a cross-sectional view of the hood in FIG. 1B.

The hood 22 may be made from a variety of pliable or conformable biocompatible materials including, but not limited to, polymeric, plastic, or woven materials that maintain enough integrity for such applications as described herein. In one example, the hood 22 can be constructed with a bulk polymer, such as polyurethane, silicon, PEBAX, PET, Nylon-12, etc. In some instances, the hood 22 can be blow molded (e.g., like a PTCA balloon) to provide maximal hoop strength with minimum material thickness. The hood 22 may be made from a translucent material and, optionally, be a variety of different colors to optimize or attenuate any reflected lighting from surrounding fluids or structures (e.g., anatomical or mechanical structures or instruments). The hood 22 may be fabricated into a uniform structure or a scaffold-supported structure, in which case a scaffold 48 (FIG. 7A) made of a shape memory alloy (e.g., Nitinol), or a spring steel, or a plastic, etc., may be fabricated and covered with a polymeric, plastic, or woven material. In one example, the scaffold 48 can comprise a helically-expanding frame.

Figure 7B:
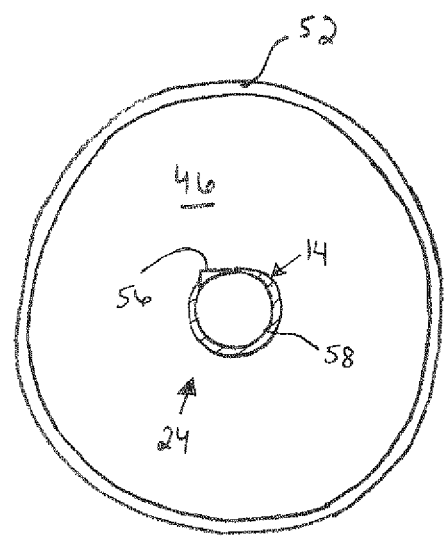
FIG. 7B is a cross-sectional view taken along Line 7B-7B in FIG. 7A.

The hood 22 can be attached at an interface 50 to the distal end portion 16 of the catheter body 14. Attachment of the interface 50 to the distal end portion 16 is proximal to the infusion ports 30 and may be accomplished through any number of conventional methods (e.g., heat or adhesive bonding). When deployed, the hood 22 can expand into any number of shapes, e.g., bell-shaped as shown, cylindrical, conical, semi-spherical, etc., provided that the open area 46 is defined by the hood. The cross-sectional shape of the hood 22 can be circular as shown in FIG. 7B; however, it will be appreciated that other cross-sectional shapes are possible (e.g., rectangular, triangular, ovoid, etc.).

The hood 22 may also define an atraumatic contact lip or edge 52 for placement or abutment against the tissue region of interest. The contact edge 52 may be made of a soft elastomeric material, such as certain soft grades of silicone or polyurethane to help the contact edge conform to an uneven or rough underlying anatomical tissue surface. In one example, the contact edge 52 can be configured to be releasably attached to a tissue (e.g., the interatrial septum) similar to a suction cup. The diameter of the hood 22 at its maximum fully deployed diameter (e.g., at the contact edge 52) is typically greater relative to a diameter of the catheter body 14. For instance, the diameter of the contact edge 52 may range anywhere from 1 to 5 times (or even greater, as practicable) a diameter of the catheter body 14. In one example, the diameter of the hood 22 at the contact edge 52 can be about 1.5 cm, which is about the half the width of the mitral valve. Moreover, the diameter of the hood 22 can be optimized based on the intended tissue to be imaged. To image inside the left atrium for an AF ablation procedure, for example, the diameter of the hood 22 can be optimized to provide a field of view sufficient for the operator of the device 10 to see the area surrounding a pulmonary vein, yet small enough to permit maneuvering within the left atrium.

In another aspect, the visualization assembly 24 can be directly connected to, and extend distally from, the distal end portion 16 of the catheter body 14. The visualization assembly 24 can be disposed within the open area 46 defined by the hood 22 so that the visualization assembly is completely enveloped or covered by the hood. For example, a distal end 54 of the visualization assembly 24 can be located proximal to the opening defined by the contact edge 52 by a distance of about 0.1 mm to about 10 mm. Alternatively, the distal end 54 of the visualization assembly 24 may be flush with the opening defined by the contact edge 52.

In some instances, the visualization assembly 24 can comprise at least one imaging element 56 that is securely connected to at least one light source 58. The imaging element 56 may be directly or wirelessly coupled to a receiver (not shown) for wireless transmission of images. Examples of imaging elements 56 can include optical fibers and CCD or CMOS imagers. Examples of light sources 58 can include optic fibers and LEDs. The visualization assembly 24 can comprise a single imaging element 56 or several imaging elements (e.g., to enable 3D imaging). In one example, the visualization assembly 24 can comprise an imager (e.g., a CMOS-ASIC camera) embedded within a high lumen LED. Advantageously, a high lumen LED can provide the illumination necessary to optimally visualize cardiac tissue structures. It will be appreciated that the visualization assembly 24 can additionally or optionally include other components, such as a transparent sheet (not shown) that overlies the lens of the imaging element 56 to prevent contact between the lens and the imaging fluid and/or the opaque fluid.

Systems

Another aspect of the present disclosure can include a system for imaging and/or manipulating a tissue. The system can comprise a device 10 (as described above) and an occlusion catheter 60 (FIGS. 8A-B) for operation in conjunction with the device. In one example, the system can comprise a device 10 that is operably connected to the occlusion catheter 60 via a CPB circuit 40 (FIG. 16). As described in more detail below, the system can be used with conventional CPB equipment to enable direct visualization of moving tissue structures (e.g., mitral valve) within a beating heart. In such instances, the system is advantageously configured to function at pressures below that needed to open the aortic valve, thereby enabling a localized replacement of blood with a translucent imaging fluid, such as saline. In operation, the CPB equipment can oxygenate blood and return it to the body to enable organ profusion. Thus, the system can provide a medical practitioner with a clear view of moving structures in a beating heart to aid in the diagnosis of disease and/or provide real-time imaging for therapy guidance.

Figure 8A:
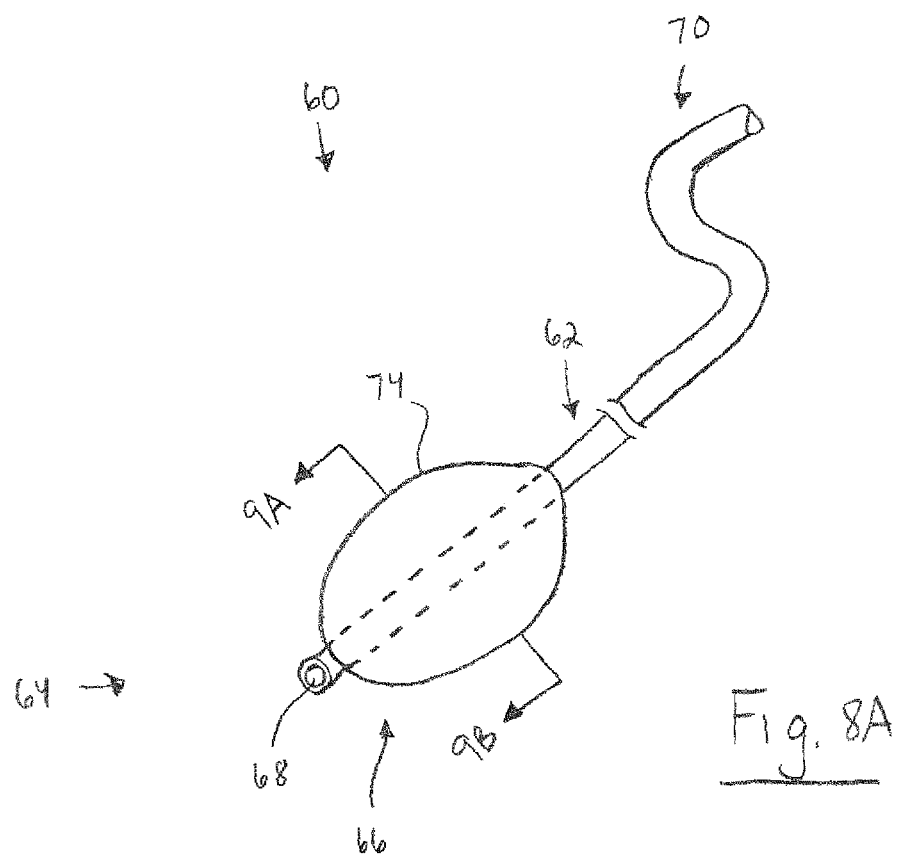
FIGS. 8A-B are perspective views showing an occlusion catheter constructed in accordance with another aspect of the present disclosure and including an inflation member in a collapsed (FIG. 8A) and expanded (FIG. 8B) configuration.
Figure 8B:
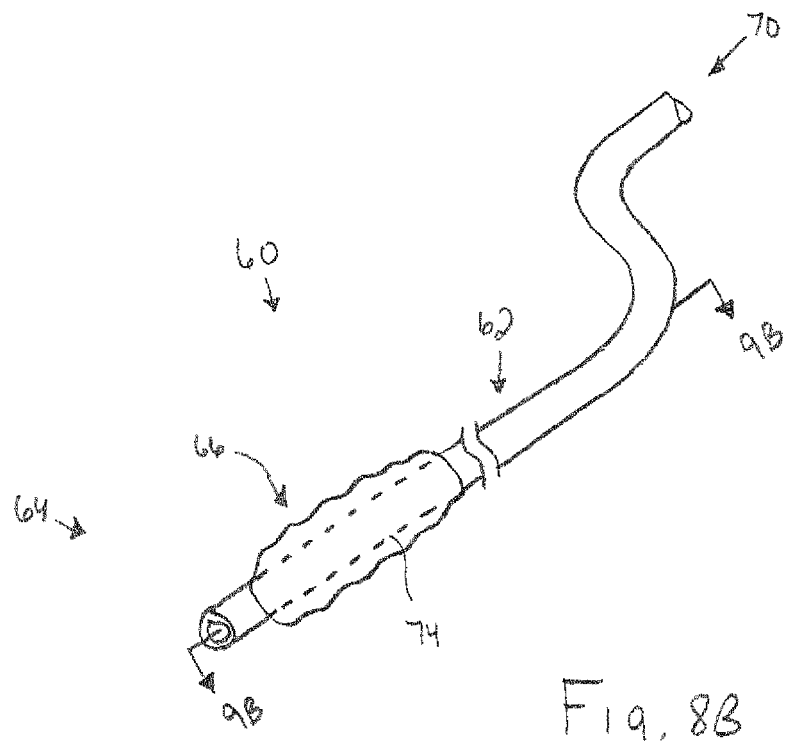

As shown in FIGS. 8A-B, the occlusion catheter 60 can comprise a main body 62 having a distal end portion 64 and at least one inflation member 66 that is operably disposed about, or connected to, the distal end portion. The main body 62 has a flexible, elongated configuration. The main body 62 includes a primary lumen 68 that extends between the distal end portion 64 and a proximal end portion 70 of the main body. The primary lumen 68 can be configured to convey a translucent imaging fluid therethrough. The proximal end portion 70 can include an interconnect (not shown) to facilitate attachment of the occlusion catheter 60 to CPB equipment. The main body 62 can be made of any one or combination of biocompatible, medical grade materials, such as a polymeric material. In some instances, the occlusion catheter 60 can be configured for insertion into a pulmonary artery to occlude blood flow into the lungs.

Figure 9A:
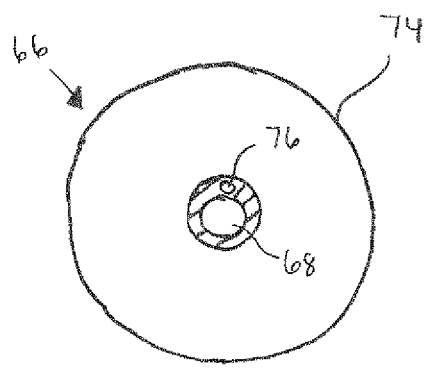
FIG. 9A is a cross-sectional view taken along Line 9A-9A in FIG. 8A.
Figure 9B:
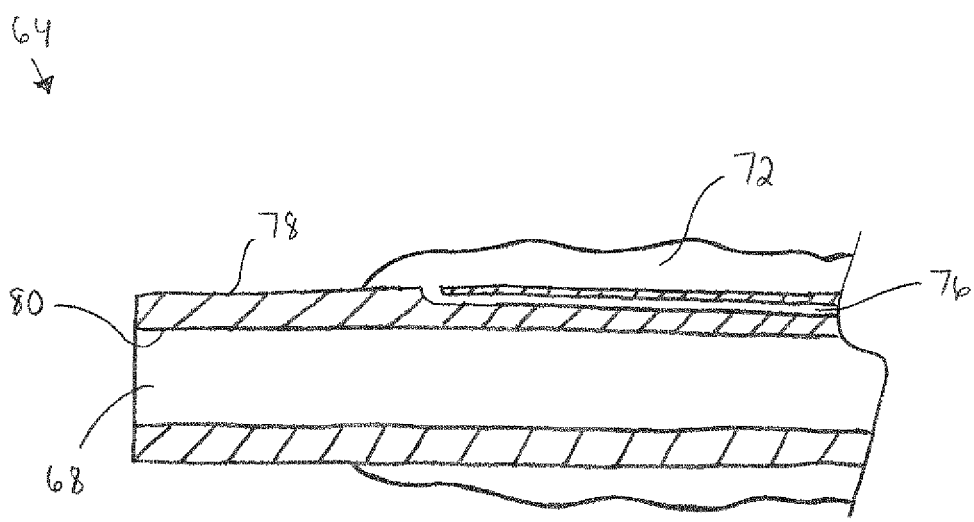
FIG. 9B is a cross-sectional view taken along Line 9B-9B in FIG. 8B.

The inflation member 66 can be configured to selectively transition between expanded and collapsed configurations. As shown in FIGS. 9A-B, the inflation member 66 can comprise a balloon having an internal lumen 72 and an outer surface 74, which is configured to sealingly contact a luminal surface of a blood vessel (e.g., a pulmonary artery) when the inflation member is in the expanded configuration. The internal lumen 72 of the inflation member 66 can be in fluid communication with a secondary lumen 76 of the main body 62. As shown in FIG. 9B, the secondary lumen 76 can extend longitudinally between an outer surface 78 and an inner surface 80 that collectively define a side wall of the main body 62. In the expanded configuration, the inflation member 66 can have a diameter of about 20 mm to about 30 mm. The inflation member 66 can be made of polyurethane or other similar elastic material(s) typically used to form biocompatible, medical grade intravascular balloons.

Methods

Figure 10:
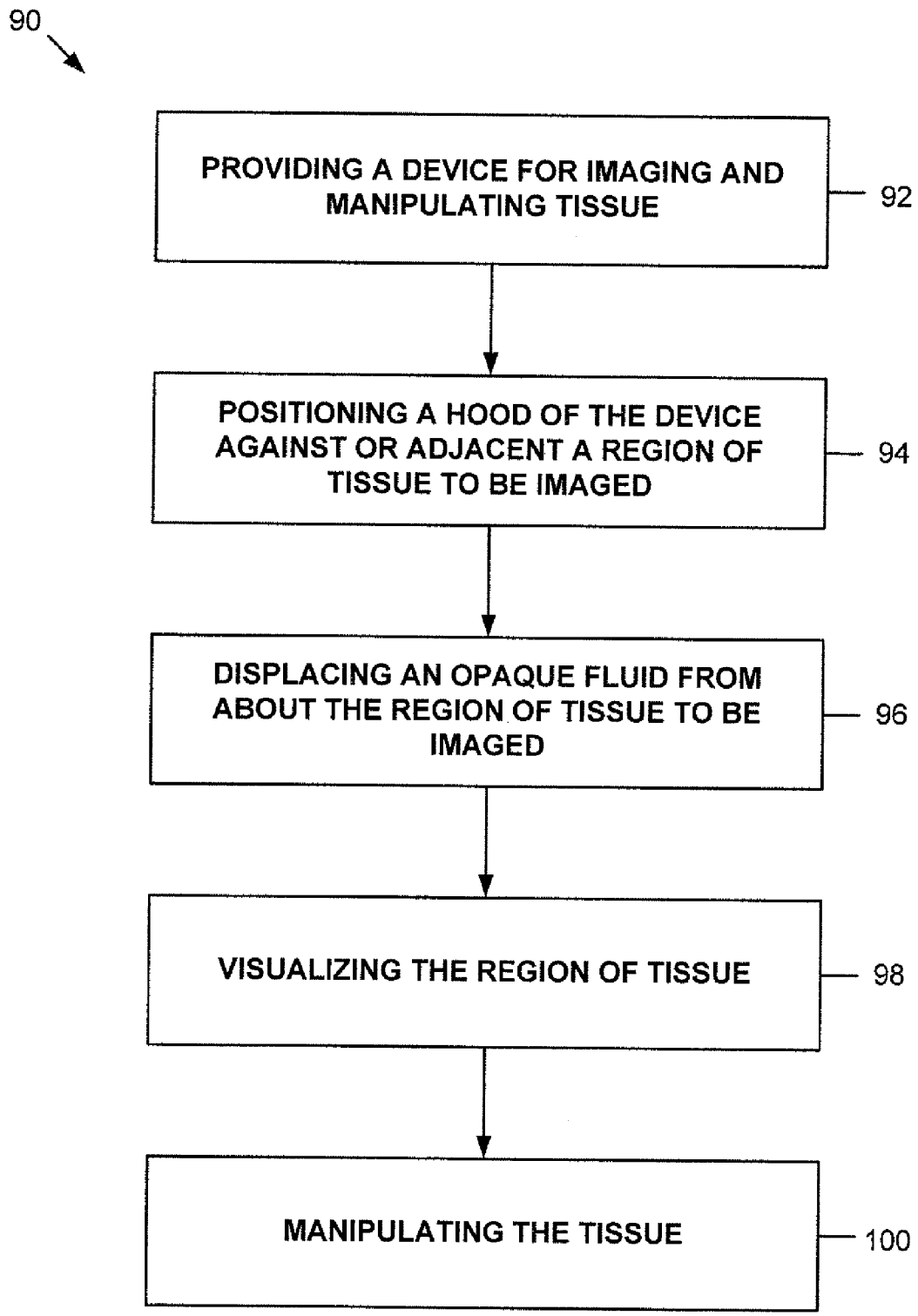
FIG. 10 is a process flow diagram illustrating a method for visualizing an immersed region of tissue according to another aspect of the present disclosure.

Another aspect of the present disclosure can include a method 90 (FIG. 10) for imaging and/or manipulating a tissue. In some instances, the method 90 can comprise the steps of: providing a device 10 or system for imaging and/or manipulating a region of tissue (Step 92); positioning a hood 22 of the device against or adjacent the region of tissue to be imaged (Step 94); displacing an opaque fluid from about the region of tissue to be imaged (Step 96); visualizing the region of tissue (Step 98); and optionally manipulating the tissue (Step 100). Although the methods of the present disclosure are described below in terms of visualizing and manipulating cardiac tissue structures, it will be appreciated that any other biological tissue or tissue structure(s) of a subject can be visualized and/or manipulated according to the methods described herein.

In some instances, Step 92 can include providing a device 10 or system as described above. One skilled in the art will appreciate that the decision of whether to use a device 10 or system of the present disclosure will depend, at least in part, on the particular tissue to be imaged, as well as other factors, such as the age of the subject, the overall health of a subject, and any existing diseases or conditions.

After selecting an appropriate device 10 or system, a portion of the device (e.g., the catheter body 14) can be surgically inserted into the subject. In some instances, methods of the present disclosure can be performed using a minimally invasive surgical procedure, such as a minithoracotomy, subxiphoid (e.g., a left ventricle approach), or percutaneous approach (e.g., via a carotid or femoral artery). Prior to surgical insertion, the catheter body 14 can be placed into a delivery catheter 12, which causes the hood 22 to obtain the low-profile delivery configuration. Once the delivery catheter 12 has been inserted into the subject, the catheter body 14 can be steered (e.g., using the handle of the device 10) until the distal end portion 16 is positioned adjacent the region of tissue to imaged.

At Step 94, the delivery catheter 12 can be progressively withdrawn to expose the distal end portion 16 of the catheter body 14. Withdrawing the delivery catheter 12 allows the hood 22 to self-expand into the expanded deployment state. With the hood 22 in the expanded deployment state, the distal end portion 16 can be further manipulated to position the contact edge 52 of the hood 22 either adjacent or against the tissue to be visualized. In some instances, the distal end portion 16 can be further manipulated before, during, or after delivery of an imaging fluid to the open area 46 of the hood 22. In such instances, one or more buttons or switches on the handle can be operated to cause the imaging fluid to be pumped (e.g., at positive pressure) through the infusion ports 30 until the fluid fills the open area 46 and displaces any fluid (e.g., blood) from within the open area (Step 96). The imaging fluid flow may be laminarized to improve its clearing effect and to help prevent blood from re-entering the hood. The imaging fluid can comprise any biocompatible fluid, e.g., saline, water, plasma, perfluorinated liquid, etc., which is sufficiently transparent to allow for relatively undistorted visualization through the imaging fluid. It will be appreciated that any number of therapeutic drugs may be suspended within the fluid or may comprise the imaging fluid itself.

Either before, during, or after opaque fluid has been displaced from the open area 46 of the hood 22, the desired region (or regions) of tissue can be visualized (Step 98). If it has not been done so already, for example, an operator (e.g., a surgeon) can activate the visualization assembly 24 using the handle of the device 10. Activation of the visualization assembly 24 can cause the light source 58 to illuminate the target tissue and provide images to the operator (via the imaging element 56). If desired, the user can choose to record the images conveyed by the imaging element 56. During visualization, the imaging fluid can be continuously flowed through the infusion ports 30 and out of the hood 22. Additionally or optionally, a negative pressure source operably connected to the device 10 can be activated to cause suction through the drainage port 26. In such instances, suctioned fluid can be removed from the subject's body or recycled (e.g., using a CPB circuit 40).

At Step 100, the visualized tissue can be optionally manipulated. In some instances, the tissue can be manipulated by inserting a medical device or tool through a lumen or working channel of the catheter body 14. A variety of medical devices or manipulation tools can be used, such as those listed above. The medical device or manipulation tool can be inserted through a port of the handle and then threaded through the catheter body 14 until a distal end of the medical device or tool extends distally through the open area 46 beyond the hood 22. One skilled in the art will appreciate that a variety of surgical procedures can be conducted using the medical device or tool, such as annular resizing, tissue ablation, PFO closure, LAA closure, placement of artificial chordae, septal punctures, repositioning existing prosthetic valves, application of sealants or valve clips, placement of sensors or electrodes, and the like.

FIGS. 11-14 illustrate one example of the method 90 in which the device 10 can be used to visualize and/or manipulate (e.g., puncture) an interatrial septum 102 of a subject. Transeptal catheterization is an established technique for obtaining accurate left heart hemodynamic and angiographic information, as well as conducting therapeutic left heart procedures. Two major problems inherent in atrial septal puncture can include cardiac perforation and puncture of an inappropriate atrial septal site. As described below, the method 90 of the present disclosure can employed to carefully and accurately visualize septal anatomy and guide surgical instruments for accurate puncture of the interatrial septum 102.

Step 92 of the method 90 can include providing a device 10 for imaging and/or manipulating the interatrial septum 102. In some instances, the device 10 can be similarly or identically constructed as described above. For example, the device 10 can include a catheter body 14, a hood 22, and a visualization assembly 24. The device 10 can further include at least one lumen 20*d* or working channel configured to receive a surgical tool 104, such as tool for puncturing the interatrial septum 102. Other additional or optional features of the device 10 are described above.

Figure 11:
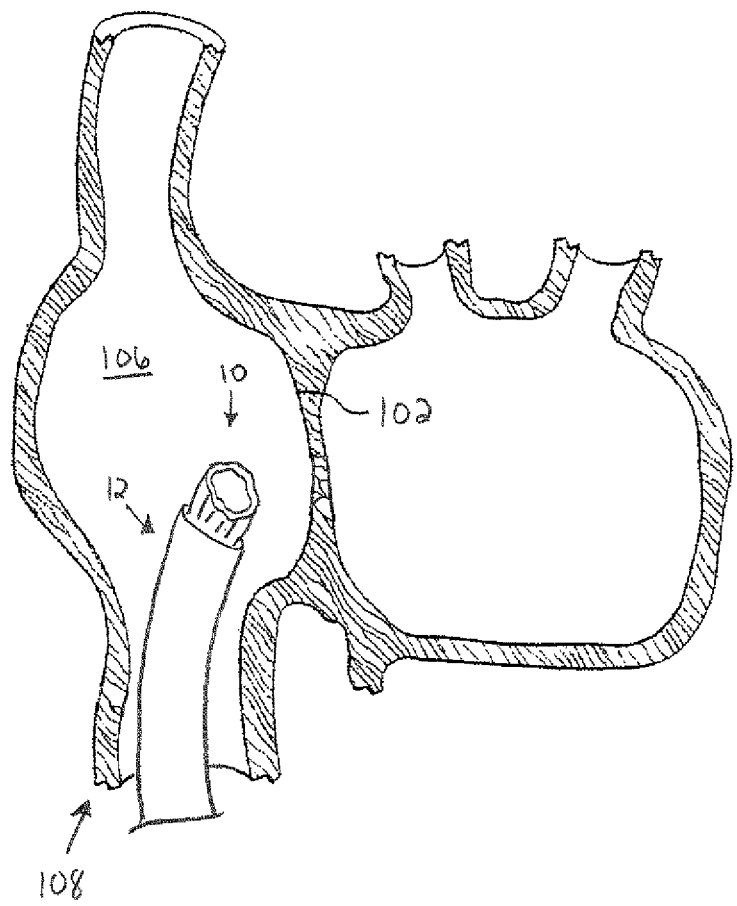
FIG. 11 is a schematic illustration showing a distal end of a delivery catheter being positioned about an interatrial septum.

To start the procedure, the device 10 can be loaded into a delivery catheter 12 such that the hood 22 obtains the collapsed configuration. The delivery catheter 12 can then be inserted into the subject at a venous access site (not shown), such as a femoral vein. Next, the delivery catheter 12 can be threaded (e.g., under image guidance) into the right atrium 106 through the inferior vena caval 08 (FIG. 11). For example, a distal end of the delivery catheter 12 can be positioned directly adjacent the interatrial septum 102 of the subject. Once the delivery catheter 102 is appropriately positioned, the delivery catheter can be progressively withdrawn from over the device 10. As the delivery catheter 12 is withdrawn, the hood 22 can self-expand into its expanded deployment state.

Figure 12:
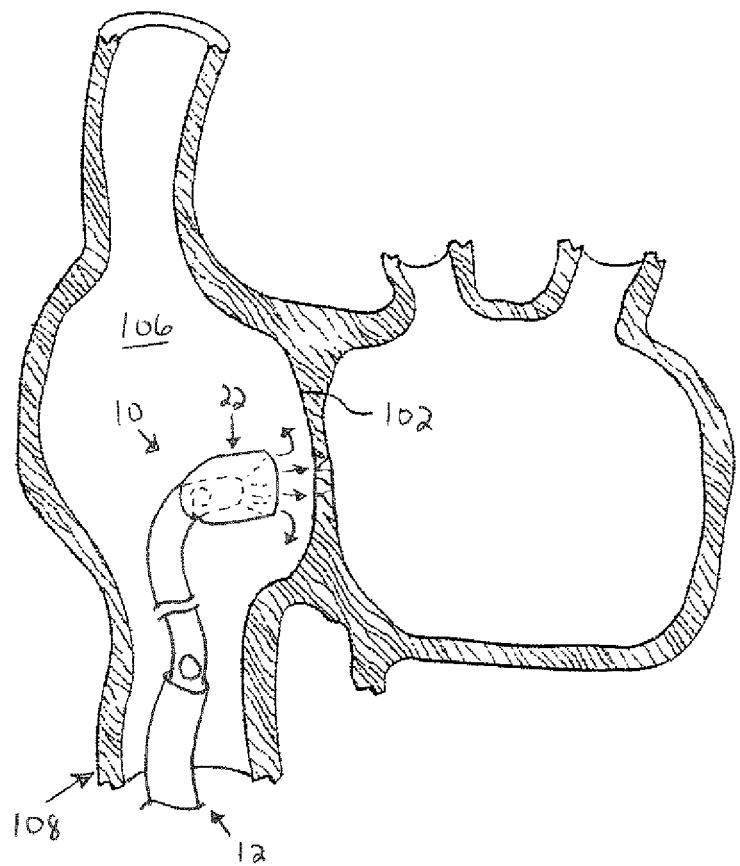
FIG. 12 is a schematic illustration showing the device in FIGS. 1A-B being deployed adjacent the interatrial septum and flowing an imaging fluid therethrough (indicated by arrows)

At Step 94, the hood 22 can be positioned against or adjacent a region of the interatrial septum 102 to be imaged. In some instances, an imaging fluid can be flowed through the device 10 (Step 96), and the visualization assembly 24 activated, when the hood 22 is adjacent (but not in contact with) the interatrial septum 102 (FIG. 12). In such instances, the distal end portion 16 of the device 10 can be steered so that the operator is able to visualize the interatrial septum 102 (Step 98). Once the desired region of the interatrial septum 102 is visible, a surgical tool 104 (e.g., a puncture needle) can be threaded through a lumen 20*d* or working channel of the device 10. With the distal end portion 14 of the device 10 appropriately positioned about the imaged region of the interatrial septum 102, the surgical tool 104 can be advanced beyond the hood 22 into contact with the interatrial septum. An axial force can then be applied to the surgical tool 104 to pierce the interatrial septum 102 and provide an access point therethrough (Step 100). The device 10 can be withdrawn and a second delivery catheter (not shown) surgically inserted into the subject to image and/or manipulate a left heart tissue structure (e.g., the mitral valve).

Figure 13:
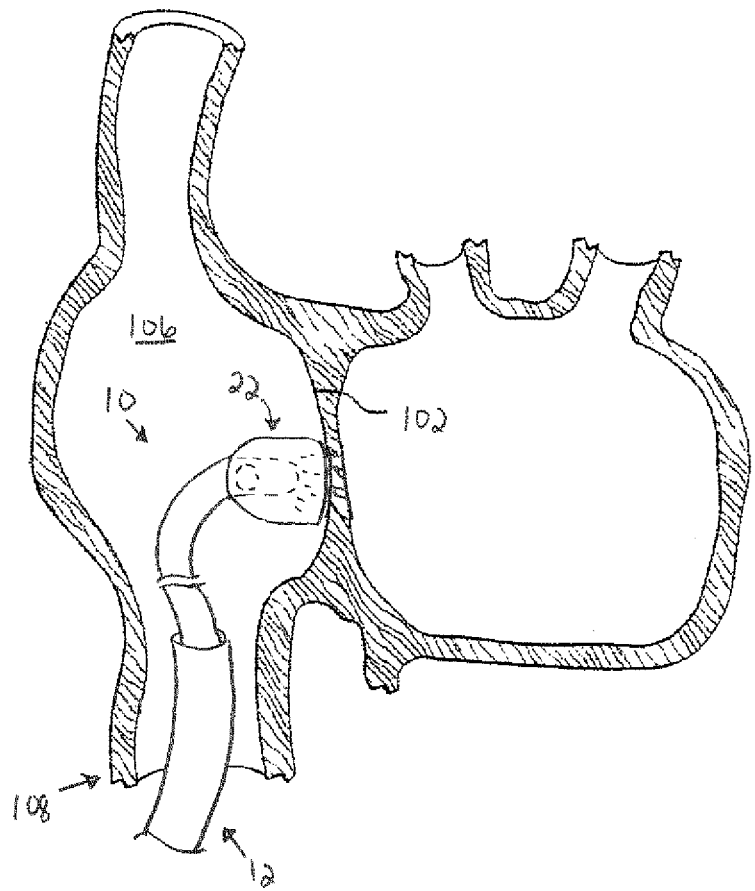
FIG. 13 is a schematic illustration showing a contact edge of the device in FIG. 12 being positioned against a region of the interatrial septum.
Figure 14:
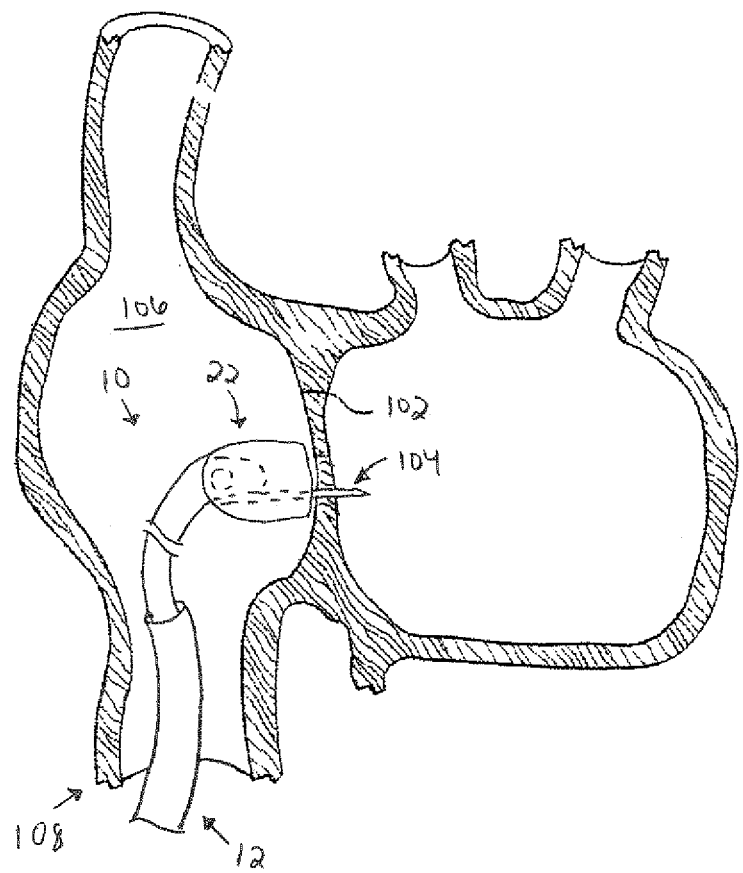
FIG. 14 is a schematic illustration showing a medical device or tool being delivered through the device in FIG. 13 to puncture the interatrial septum.

In other instances, the hood 22 (e.g., the contact edge 52) can be pressed against a region of the interatrial septum 102 so that a seal (e.g., similar to a suction cup) is formed between the region and the contact edge. In such instances, an imaging fluid can be flowed through the device 10 while also operating the visualization assembly 24 to visualize the region of the interatrial septum 102 (Step 98) (FIG. 13). Without breaking the seal formed between the region and the contact edge 52, the distal end portion 16 of the device 10 can then be moved about the interatrial septum 102 to image other regions. Once the hood 22 is appropriately positioned about a desired region, a surgical tool 104 (e.g., a puncture needle) can be threaded through a lumen 20*d* or working channel of the device 10. The surgical tool 104 can then be advanced beyond the hood 22 into contact with the interatrial septum 102. As shown in FIG. 14, an axial force can be applied to the surgical tool 104 to pierce the interatrial septum 102 and provide an access point (Step 100). The device 10 can be withdrawn and a second delivery catheter (not shown) surgically inserted into the subject to image and/or manipulate a left heart tissue structure (e.g., mitral valve).

Figure 15:
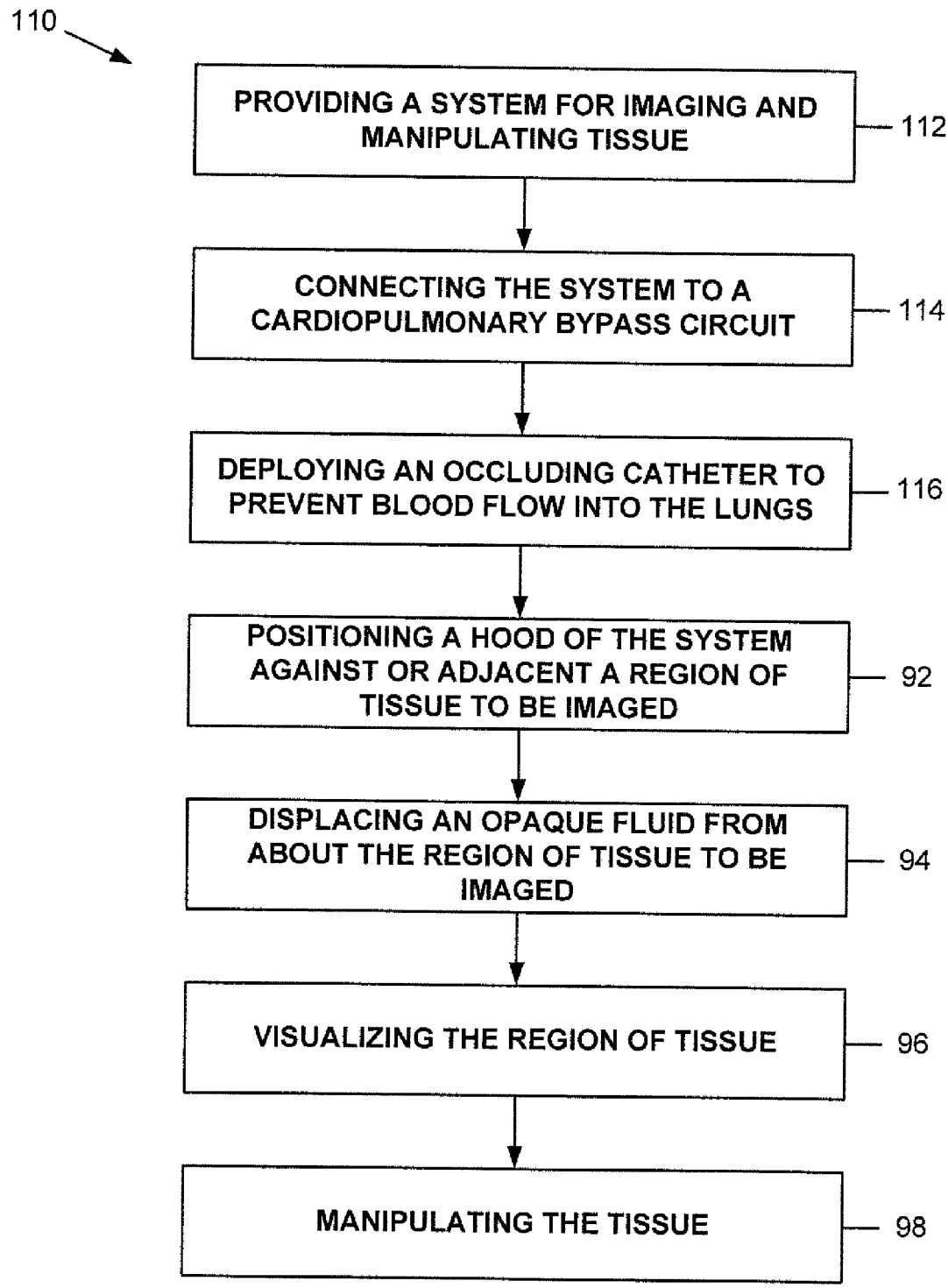
FIG. 15 is a process flow diagram illustrating a method for visualizing an immersed region of tissue according to another aspect of the present disclosure.
Figure 17:
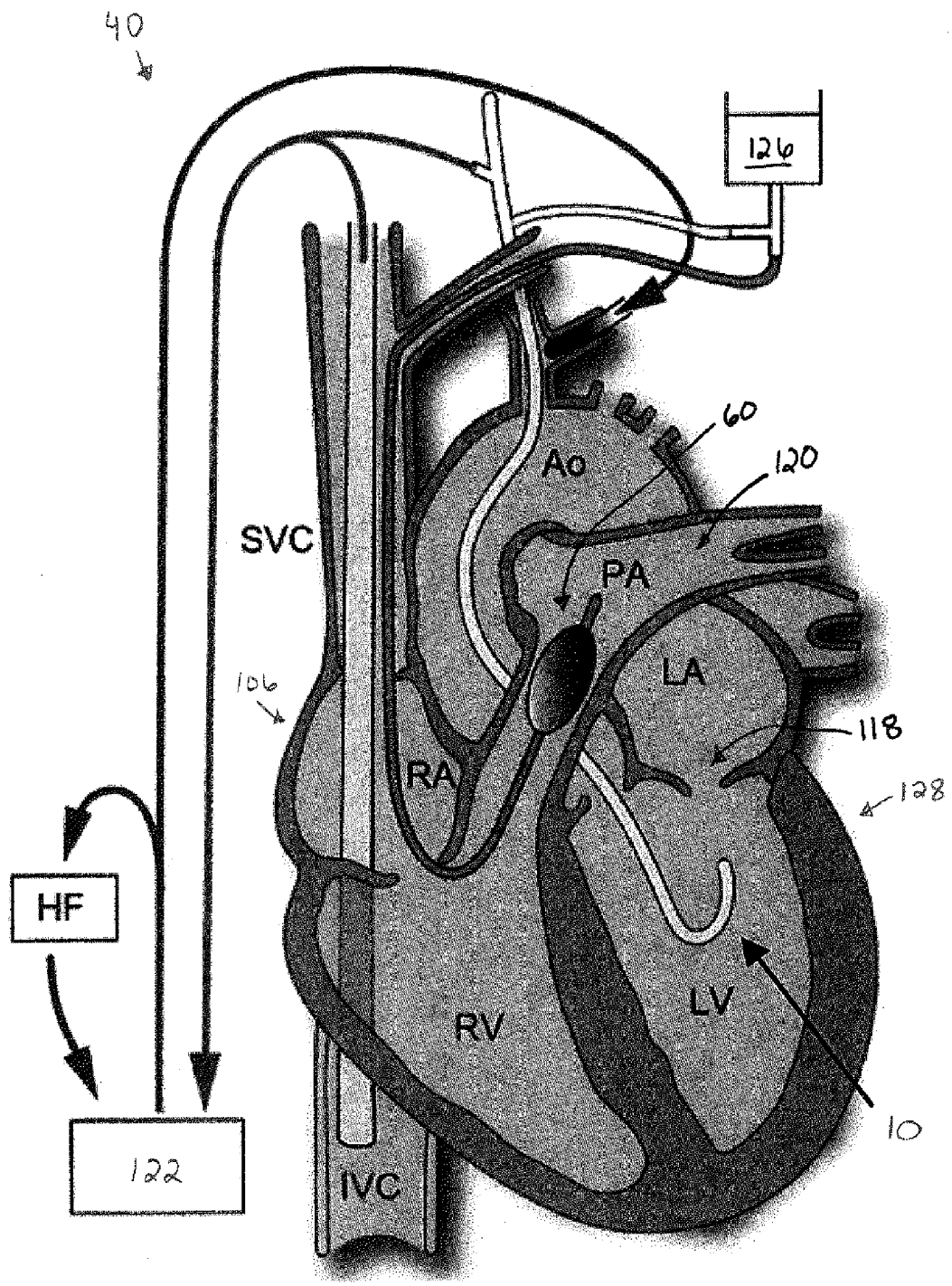
FIG. 17 is a schematic illustration showing use of the system and CPB in FIG. 16 to visualize immersed mitral valve via a percutaneous approach.

Another aspect of the present disclosure can include a method 110 (FIG. 15) for imaging and/or manipulating an immersed region of tissue. Steps that are identical or nearly identical to those in FIG. 10 use the same reference numbers, whereas steps that are different than those in FIG. 10 use different reference numbers. In one example, the method 110 can be used to visualize and/or manipulate a cardiac tissue or structure, such as a mitral valve 118. Although access to the mitral valve 118 is described and illustrated herein as being performed via an arterial puncture technique, it will be appreciated that various other minimally invasive surgical approaches can be used, such as a percutaneous approach (FIG. 17) as well as those described above.

At Step 112 (FIG. 15), the method 110 can include providing a system for imaging and/or manipulating tissue. The system can be identically or similarly constructed as the system described above. For example, the system can comprise a device 10 and an occlusion catheter 60. In some instances, the occlusion catheter 60 can include an inflation member 66 configured for placement in a pulmonary artery 120. The proximal end portion 18 of the catheter body 14 and the proximal end portion 70 of the occlusion catheter 60 can each be operably connected to a CPB circuit 40 as shown in FIG. 16 (Step 114). The CPB circuit 40 can include a venous return 122, an arterial return 124, and a pump 126. Other components of the CPB circuit 40, such as venous and arterial return catheters can be placed as shown in FIG. 16. If it has not been done so already, the occluding catheter 60 can be implanted in pulmonary artery 120 of the subject to prevent blood flow into the lungs (Step 116).

Once the occluding catheter 60 has been appropriately positioned, Steps 92-98 of the method 110 can be performed as described above. Using an arterial puncture site, for example, the distal end portion 16 of the device 10 can be advanced through the left ventricle 128 to a position directly adjacent the mitral valve 118. In some instances, the CPB circuit 40 can be operated as described by Mihaljevic, T. et al., *J Thorac Cardio Surg.* 142(1):199-202 (2011). With the CPB circuit 40 activated, an operator can activate the device 10 so that imaging fluid is flowed through the hood 22 towards the mitral valve 118 at a desired flow rate (e.g., about 1 L/min). As the imaging fluid displaces blood from about the mitral valve 118, suction can be applied so that opaque fluid (e.g., blood) is continuously removed from the left ventricle 128 by the drainage port 26. The operator can then readily visualize the mitral valve 118 and/or perform additional steps to manipulate the mitral valve.

Advantageously, the system, when used with conventional CPB equipment, enables direct visualization of moving structure within a beating heart. The system is configured to function at pressures below that needed to open the aortic valve (e.g., less than about 20 mm Hg), thereby enabling a localized replacement of blood with the imaging fluid. The heart flows about five liters of blood per minute. For conventional imaging catheters, there is simply too much blood coursing through the heart for such catheters to deliver sufficient fluid to displace all the blood in front of the camera. The present method 110 permits bypass of all five liters of blood each minute simultaneously with selective delivery of an imaging fluid in front of the imaging element 56 to enhance image quality. In doing so, the method 110 can advantageously provide a clear view of the mitral valve 118 in a beating heart to aid in the diagnosis of mitral valve disease or provide real-time imaging for therapy guidance.

From the above description of the present disclosure, those skilled in the art will perceive improvements, changes and modifications. Such improvements, changes, and modifications are within the skill of one in the art and are intended to be covered by the appended claims.

The following is claimed:

1. A system for imaging a tissue comprising:
    a device including:
        a catheter body having a distal end portion, a proximal end portion, and at least one lumen extending between said distal and proximal end portions, said catheter body including at least one drainage port having a first opening and at least one infusion port having a second opening, said first and second openings being located about a lateral aspect of said catheter body;
        a hood projecting distally from said distal end portion and being configured to self-expand into an expanded deployment state defining an open area therein; and
        a visualization assembly disposed within said open area and extending distally from said distal end portion of said catheter body; and
    an occlusion catheter comprising:
        a main body having a distal end portion, a proximal end portion, and lumen that extends between said distal and proximal end portions; and
        an inflation member operably disposed about said distal end portion and being configured to selectively transition between expanded and collapsed configurations, said inflation member having an outer surface configured to sealingly contact a luminal surface of a blood vessel when said inflation member is in the expanded configuration;
    wherein said proximal end portion of said main body includes a port adapted for connection to a cardiopulmonary bypass (CPB) circuit.

2. The system of claim 1, wherein said inflation member is shaped and configured for placement in a pulmonary artery to prevent blood flow into the lungs when said inflation member is in the expanded configuration.

3. A method for imaging an immersed region of tissue, said method comprising the steps of:
    providing a device that includes a catheter body, a hood, and a visualization assembly, the catheter body having a distal end portion, a proximal end portion, and at least one lumen extending between the distal and proximal end portions, the catheter body including at least one drainage port having a first opening and at least one infusion port having a second opening, the first and second openings being located about a lateral aspect of the catheter body, the hood projecting distally from the distal end portion of the catheter body and being configured to self-expand into an expanded deployment state defining an open area therein, the visualization assembly being disposed within the open area and extending distally from the distal end portion of the catheter body;
    providing an occlusion catheter that includes a main body and an inflation member, the main body having a distal end portion, a proximal end portion, a lumen that extends between the distal and proximal end portions, the inflation member being operably disposed about the distal end portion, the proximal end portion being operably connected to a CPB circuit;
    coupling the proximal end portion of the catheter body to the CPB circuit;
    placing a portion of the occlusion catheter in a pulmonary artery;
    inflating the inflation member so that an outer surface thereof sealingly contacts a luminal surface of the pulmonary artery to prevent blood flow into the lungs;
    positioning the hood against or adjacent the region of tissue to be imaged;
    urging a translucent imaging fluid into the open area of the hood via the second opening such that an opaque fluid is displaced from within the open area into the environment external to the hood; and
    operating the CPB circuit to visualize the region of tissue through the translucent imaging fluid using the visualization assembly.

4. The method of claim 3, wherein said step of positioning the hood further includes advancing the catheter body intravascularly into a chamber of a heart.

5. The method of claim 3, wherein said step of positioning the hood further comprises deploying the hood from a low-profile delivery configuration into the expanded deployment state.

6. The method of claim 3, wherein said step of urging a translucent imaging fluid further comprises pumping the imaging fluid into the hood through a fluid delivery lumen defined through the catheter body.

7. The method of claim 3, wherein said step of urging a translucent imaging fluid further comprises urging saline, plasma, water, or perfluorinated liquid into the hood such that blood is displaced from the open area of the hood.

8. The method of claim 3, further comprising treating the region of tissue with a therapeutic tool advanced through the catheter body.

9. The method of claim 3, further comprising sensing a physiological parameter within or outside of the hood using a sensor advanced through the catheter body.

\* \* \* \* \*